United States Patent [19]
Klaassen et al.

[11] Patent Number: 6,159,725
[45] Date of Patent: *Dec. 12, 2000

[54] TRANSFORMED YEAST STRAINS

[75] Inventors: Paul Klaassen, Dordrecht; Rutger Jan Van Rooijen, Ede, both of Netherlands

[73] Assignee: Gist-brocades, B.V., Es Delft, Netherlands

[ * ] Notice: This patent issued on a continued prosecution application filed under 37 CFR 1.53(d), and is subject to the twenty year patent term provisions of 35 U.S.C. 154(a)(2).

[21] Appl. No.: 08/783,045

[22] Filed: Jan. 16, 1997

[30] Foreign Application Priority Data

Jan. 16, 1996 [EP] European Pat. Off. .............. 96200074

[51] Int. Cl.[7] .............................. C12N 1/16; C12P 21/06
[52] U.S. Cl. ..................... 435/254.21; 435/69.1; 435/254.11; 435/254.2; 435/254.21; 435/255.1; 435/255.2; 435/255.21
[58] Field of Search ........................ 435/254.11, 254.2, 435/254.21, 69.1, 255.1, 255.2, 255.21

[56] References Cited

U.S. PATENT DOCUMENTS 5,190,877 3/1993 Osinga et al. ..................... 435/256

FOREIGN PATENT DOCUMENTS 0 577 915 A1 1/1994 United Kingdom .

OTHER PUBLICATIONS

Bell, W. et al. *Eur J Biochem* (1992) 209:951–959.
Bennetzen, J.C. et al. *J Biol Chem* (1982) 257:3018.
de Winde, J.H. et al. *Eur J Biochem* (1996) 241:633–643.
Gritz, L. et al. *Gene* (1983) 25:179–188.
Hohmann, S. et al. *Curr Genet* (1993) 23:281–289.
Holland and Holland *J Biol Chem* (1980) 255:2596–2605.
Ito, H. et al. *J. Bacteriology* (1983) 153:163–168.
Lagunas, R. *FEMS Microbiol Rev* (1993) 104:229–242.
Londesborough, J. et al. *J Gen Micr* (1991) 137:323–330.
Reifenberger, E. et al. (1995) 16(1):157–167.
Smits, H.P. et al. *Yeast* (1996) 12:439–447.
Szostak, J.W. et al. *Plasmid* (1979) 2:536.
Thevelein, J.M. *Ant V Leeuwenh* (1992) 62:109–130.
Thevelein, J.M. et al. *TIBS* (1995) 20:3–10.
van Dam, K. et al. *Ant V Leeuwenh* (1993) 63:315–321.
George Theodoris et al., "High–Copy Suppression of Glucose Transport Defects by HXT4 and Regulatory Elements in the Promoters of the HXT Genes in *Saccharomyces cerevisiae*," Genetics, vol. 137, No. 4, Aug. 1994, pp. 957–966.

*Primary Examiner*—Christina Y. Chan
*Assistant Examiner*—Mary Beth Tung
*Attorney, Agent, or Firm*—Morrison & Foerster LLP

[57] ABSTRACT

Transformed yeasts are provided which constitutively express a hexose transporter gene. The transformed yeast can be used in the beer, bread, wine and whisky production.

10 Claims, 6 Drawing Sheets

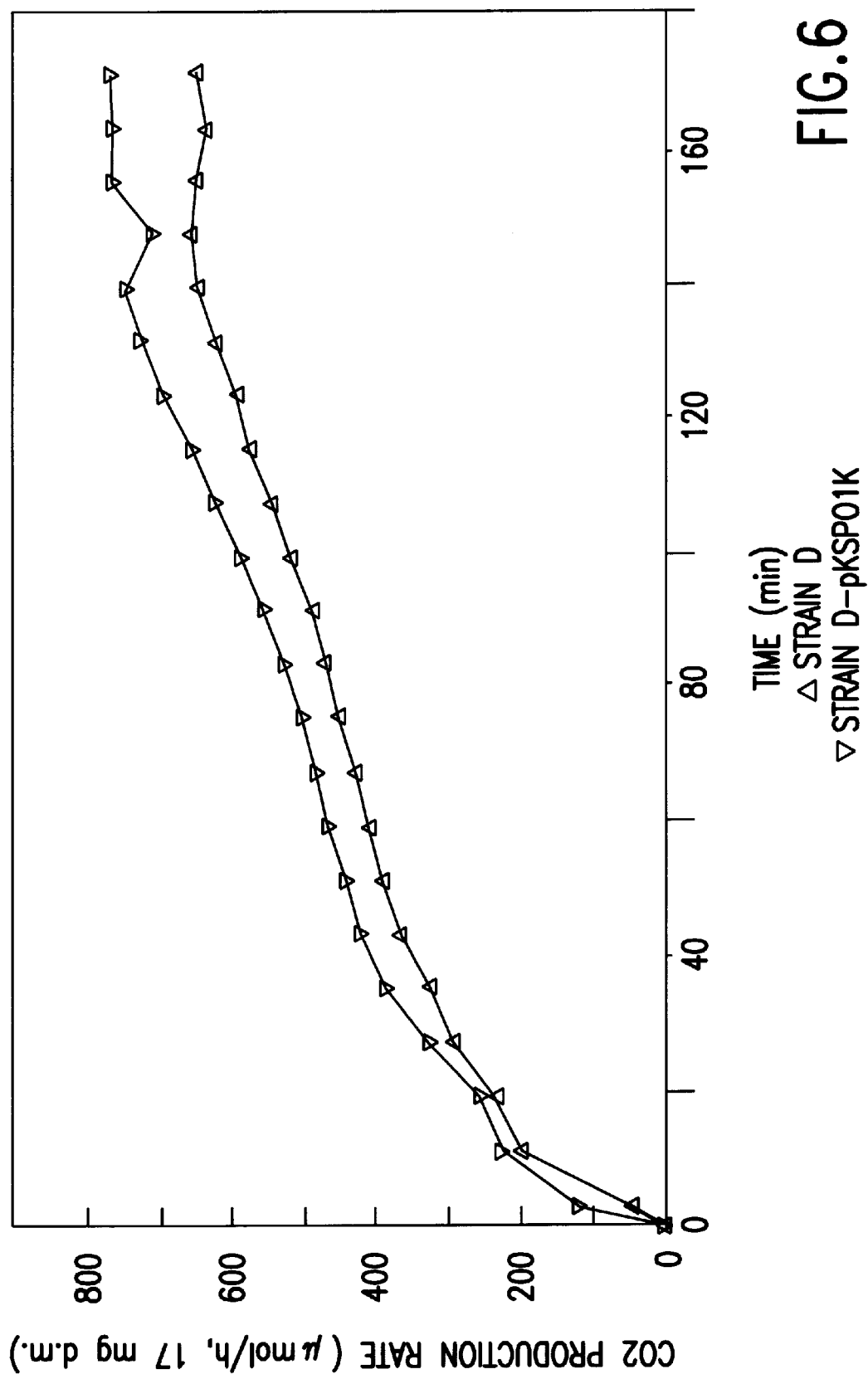

TRANSFORMED YEAST STRAINS

The present invention relates to improvement of gas and alcohol production by yeast.

Yeast strains for example belonging to the genus Saccharomyces are used worldwide in the production of ethanol and leavening of bread. Such yeasts are capable of fermenting sugars to approximately equimolar amounts of carbondioxide ($CO_2$) and ethanol under anaerobic conditions. Baker's yeast is commercially available as cream yeast (15%–21% dry matter), compressed yeast (26%–33% dry matter), active dry yeast (92%–94% dry matter) or instant dry yeast (94%–97% dry matter). The past decades, one of the most important goals in yeast research has been the improvement of the fermentative capacity of baker's yeast, resulting in improved $CO_2$-production rates. For this purpose, both classical hybridisation and molecular genetic techniques have been applied.

One of the early steps in the metabolism of sugars by the action of yeast is the transport of the sugars across the plasma membrane. Specific carriers for different sugars are expressed in yeast. In Saccharomyces, the uptake of hexoses, such as glucose and fructose, is mediated by specific hexose transporters which belong to a superfamily of monosaccharide facilitators (Reifenberger, E., Freidel, K. and Ciriacy, M. (1995) 16(1), 157–167). To date, more than sixteen genes encoding such carriers, notably the so-called HXT-genes (which stands for hexose transport), have been identified. The expression of individual HXT-genes and homologues is dependent on environmental factors, such as the hexose concentration sensed by the yeast cell. It has been proposed that the uptake of hexoses is catalysed by two kinetically different systems (Bisson, L. F., Coons, D. M., Kruckeberg, A. L. and Lewis D. A. (1993) Crit Rev Biochem Mol Biol 28, 295–308; Lagunas, R. (1993) FEMS Microbiol Rev 104, 229–242). One system has a high affinity for hexoses. This high affinity component is absent in cells growing in relatively high hexose concentrations, e.g. 2% glucose. Under these conditions, low affinity transporters are being expressed by the yeast cell. Construction of mutant yeast strains lacking multiple HXT genes has made it possible to identify the main glucose transporters in yeast (Reifenberger et al, supra). In a yeast strain lacking the genes HXT1 through HXT7, growth on media containing high and low glucose concentrations (0.1% to 5%), glucose uptake and glucose consumption were below the detection level. In mutant yeast strains expressing only one of the genes HXT1 through HXT7, it was shown that Hxt1p and Hxt3p are low-affinity transporters ($k_m \approx$ 50–100 mM hexose), Hxt4p is moderately low, and Hxt2p, Hxt6p and Hxt7p are high affinity transporters ($k_m \approx$ 1–4 mM hexose), regardless of the culture conditions of these mutants (0.1% or 5% glucose) (Reifenberger, E., Freidel, K. and Ciriacy, M. (1995) Yeast 11, S457).

In the literature, a mutant of a laboratory strain, affected in glucose uptake has been described. The gene encoding this mutation was named GGS1 (Thevelein, J. M. (1992) Ant.V.Leeuwenh. 62, 109–130). Thevelein proposed the following model: in wild-type cells, glucose influx is mediated by a complex consisting of a low affinity glucose carrier, a sugar kinase and the GGS1-gene product (or a protein controlled by GGS1). The complex was suggested to have two functions: i) restraining and regulating glucose influx, and ii) activation of a whole series or all glucose-induced signalling pathways. According to the model, in a ggs1 mutant, the complex is no longer functional, leading to a metabolic imbalance: the cells stop growing because a rapid build-up of sugar phosphates inside the cells resulting in inorganic phosphorous ($P_i$) depletion.

However, the observed defects in signalling could be restored by deletion of the HXK2-gene, encoding hexokinase PII (Hohmann, S., Neves, M. J., de Koning, W., Alijo, R., Ramos, J. and Thevelein, J. M. (1993) Curr. Genet. 23, 281–289). Apparently, the high rate of the first steps in the glycolysis is reduced by the slower rate of hexose phosphorylation. This conclusion is also supported by the observation that a ggs1-mutant is able to grow in the chemostat, where the influx of glucose into the cells is limited by the amount of sugar in the medium (van Dam, K., Jansen, N., Postma, P., Richard, P., Ruijter, G., Rutgers, M., Smits, H. P., Teusink, B., van der Vlag, J., Walsh, M. C., Westerhoff, H. V. (1993) Ant.V.Leeuwenh. 63, 315–321). The fact that in a ggs/hxk double mutant laboratory strain glucose signalling effects are present, indicates that the GGS protein itself cannot be the signalling molecule. Moreover, it turned out that the GGS1-gene is identical to the TPS1-gene, encoding trehalose-6-phosphate synthase (Bell, W., Klaassen, P., Ohnacker,M., Boller, T., Herweijer, M. A., Schoppink, P. J.van der Zee, P., Wiemken, A. (1992) Eur.J.Biochem. 209, 951–959). Three possible models which may account for the interaction between a hexose transporter, hexose phosphorylating enzyme and the trehalose synthesizing complex have been proposed (Thevelein, J. M., Hohmann, S. (1995) TIBS 20, 3–10). Each of the models is able to explain some observations, none of the models however is definitely established nor supported by experimental evidence.

In yeast cells of a laboratory strain lacking all three hexose kinases (hxk1, hxk2, glk1) it was shown that glucose is still transported across the plasma membrane (Smits, H. P., Smits, G. J., Postma, P. W., Walsh, M. C. and van Dam, K. (1996) Yeast 12, 439–447). The intracellular glucose concentration accumulated up to 2.0 mM, showing that glucose transport still occured, despite the absence of hexose kinases.

The purification of the whole trehalose synthase complex, as well as the TPS1 (GGS1) protein has been described (Londesborough, J. and Vuorio, O. (1991) J.Gen.Micr. 137, 323–330; Bell, W., Klaassen, P., Ohnacker,M., Boller, T., Herweijer, M. A., Schoppink, P. J.van der Zee, P., Wiemken, A. (1992) Eur.J.Biochem. 209, 951–959). The trehalose synthase complex was purified from the cytosolic fraction, strongly suggesting that GGS1 is not a membrane associated protein.

All together, it may be concluded that the model proposing the interaction between a low affinity glucose carrier, a sugar kinase and the GGS1-gene product (Thevelein, J. M. (1992) Ant.V.Leeuwenh. 62, 109–130) is still rather speculative. Recently, the Thevelein-group also questioned their initial model (de Winde, J. H., Crauwels, M. Hohmann, S., Thevelein, J. M. and Winderinckx, J. (1996) Eur.J.Biochem.241, 633–643).

Surprisingly, we have now found that industrial yeasts constitutively expressing one or several genes involved in the transport of hexoses, for instance as a result of the introduction of extra copies of HXT-genes under control of a constitutive promoter, results in new strains with improved $CO_2$ and ethanol production rates. It is known that large improvements in performance can easily be obtained in haploid (laboratory) strains. In industrial and commercially available strains however, this is much more difficult. The present industrial and commercially available yeast strains have been improved over several decades using classical genetic techniques. It is believed that industrial strains are already performing at their near maximum gas production rate.

Effects on the hexose uptake rate, and hence the gas production, may also be obtained by mutation of the natural promoters of the hexose transporter genes, for instance by deletion, insertion or substitution of one or more nucleotides in the promoter region, such that the expression of the hexose transporter gene concerned is altered.

The present invention provides a transformed yeast, improved in the fermentation rate of hexoses. In order to construct such a yeast, at least one, preferably homologous, DNA construct which comprises at least one HXT-gene or homologue encoding a protein facilitating the uptake of hexoses, preferably under control of a constitutive strong promoter, is introduced into the yeast. We found that advantageously low-affinity transporter genes are used ($k_m$ = 20–100 mM). Preferably HXT1 and/or HXT3 genes are used. Said genes may be introduced into the yeast cells and stably maintained by integration into the host cell genome. Alternatively, the DNA constructs may be maintained on non-integrative vectors, such as plasmids, preferably multi-copy plasmids.

The industrial yeast production process consists of culturing baker's yeast in a fed batch fermenter. Often, molasses is used as a carbon source. The yeast product contains several, but not all, hexose transporters, i.e. those which were of importance in the fed batch fermentation process. These hexose transporters are not the same as those that are needed by the yeast in dough, because of differences in environmental conditions. As a consequence, the yeast needs to adapt itself to the new environment by synthesizing the right set of hexose transporters. In the yeasts according to the present invention, the right set of hexose transporters for application in dough is expressed immediately.

Therefore according to one aspect of the invention the HXT-gene or homologue is expressed under conditions wherein this gene is not expressed by the wild-type strain under these conditions.

The invention provides a transformed yeast strain which has a hexose transporter gene which is immediately expressed when the yeast is added to the dough, whereas the wild-type strain needs a long period of time e.g. 30 to 45 minutes before the wild-type strain is able to express this gene in sufficient amounts.

By hexose is meant any sugar or carbohydrate having six carbon atoms, for example glucose, fructose, galactose or mannose.

By hexose transporter gene is meant a gene encoding a protein which facilitates the diffusion of hexoses across the plasma membrane, for example the HXT1, HXT2, HXT3, or HXT4 genes. DNA sequences derived from these genes by substitution, deletion or addition of one or more nucleotides in such a way that the DNA sequence still encodes a protein capable of transporting hexose(s) are considered to be a part of this invention.

By industrial yeast is meant any yeast strain that is not a haploid yeast strain and having a $CO_2$-production of more than 450 ml $CO_2$ per 285 mg dry matter in 165 minutes in test A, preferably 500 ml $CO_2$ per 285 mg dry matter in 165 minutes in test A. Preferably the industrial yeast is baker's yeast, more preferably a yeast belonging to the genus Saccharomyces, and even more preferably a strain of *Saccharomyces cerevisiae*.

By homologous DNA is meant DNA originating from the same yeast genus. For example, homologous DNA is used when Saccharomyces is transformed with DNA originating from Saccharomyces. Thus, the hexose transporter gene and any promoter used to effect its expression are preferably homologous to the yeast to be transformed. Preferably, any other DNA introduced with the gene and promoter, if present, is also homologous. In this way, the existing properties of the yeast genus will be improved, without introducing new properties originating from another genus. The genes of interest include those encoding sugar carriers, particularly hexose transporters, homologous genes, or DNA sequences derived from these sequences by substitution of one or more nucleotides, or by addition or deletion of one or more codons, in such a way that the altered DNA sequence still encodes a protein capable of transporting a hexose.

By a constitutive promoter is meant a promoter which effects expression of a gene independently of environmental conditions, for example the alcohol dehydrogenase promoter (ADH1-promoter), similar to that described by Bennetzen and Hall (Bennetzen, J. C. and Hall, B. D. (1982) J.Biol.Chem. 257, 3018), the glyceraldehyde-3-phosphate dehydrogenase promoter (GAPDH-promoter), similar to that as described by Holland and Holland (Holland and Holland, (1980), J.Biol.Chem. 255 2596–2605); as well as HXT-promoters that have been mutated by deletion, insertion or substitution of one or more nucleotides. Use of such a promoter effects expression under the conditions of fed-batch fermentation production processes as well as under dough conditions.

The transformed yeast according to this invention can be used as a starting strain for strain improvement procedures, such as mutation, mass mating and protoplast fusion. The resulting strains are considered to form part of this invention.

After introduction of genes enhancing the uptake of hexoses as described above, an increase in gas production may be observed in doughs containing varying amounts of sugar (from 0% sucrose up to about 30% sucrose).

The invention not only applies to dough, but to any fermentation process, for example fermentation systems for industrial ethanol production from hydrolysed starch. Transformed yeasts strains of this invention therefore include not only strains of baker's yeast, but also, for example, beer, whisky and wine yeast strains.

The present inventors have thus established that introduction of constructs containing hexose transporter genes and/or homologues thereof under control of strong constitutive promoters can be advantageously employed to increase the hexose uptake rate, and hence the gas production rate in doughs. The example below illustrates the invention with reference to baker's yeast overexpressing hexose carriers.

LEGENDS TO THE FIGS.

FIG. 6 shows the gas production rates of strain D and a transformant of strain D constitutively expressing Hxt1p.

CLONING TECHNIQUES

For general cloning techniques reference is made to the handbook of Sambrook et al (Sambrook, J., Fritsch, E. F. and Maniatis, T. (1989) Molecular cloning: a laboratory manual. Cold Spring Harbor Laboratory Press, Cold Spring Harbor, N.Y.).

Construction of Recombinant Plasmids
1) pTZ18RGAPDHhygB

Figure 1:
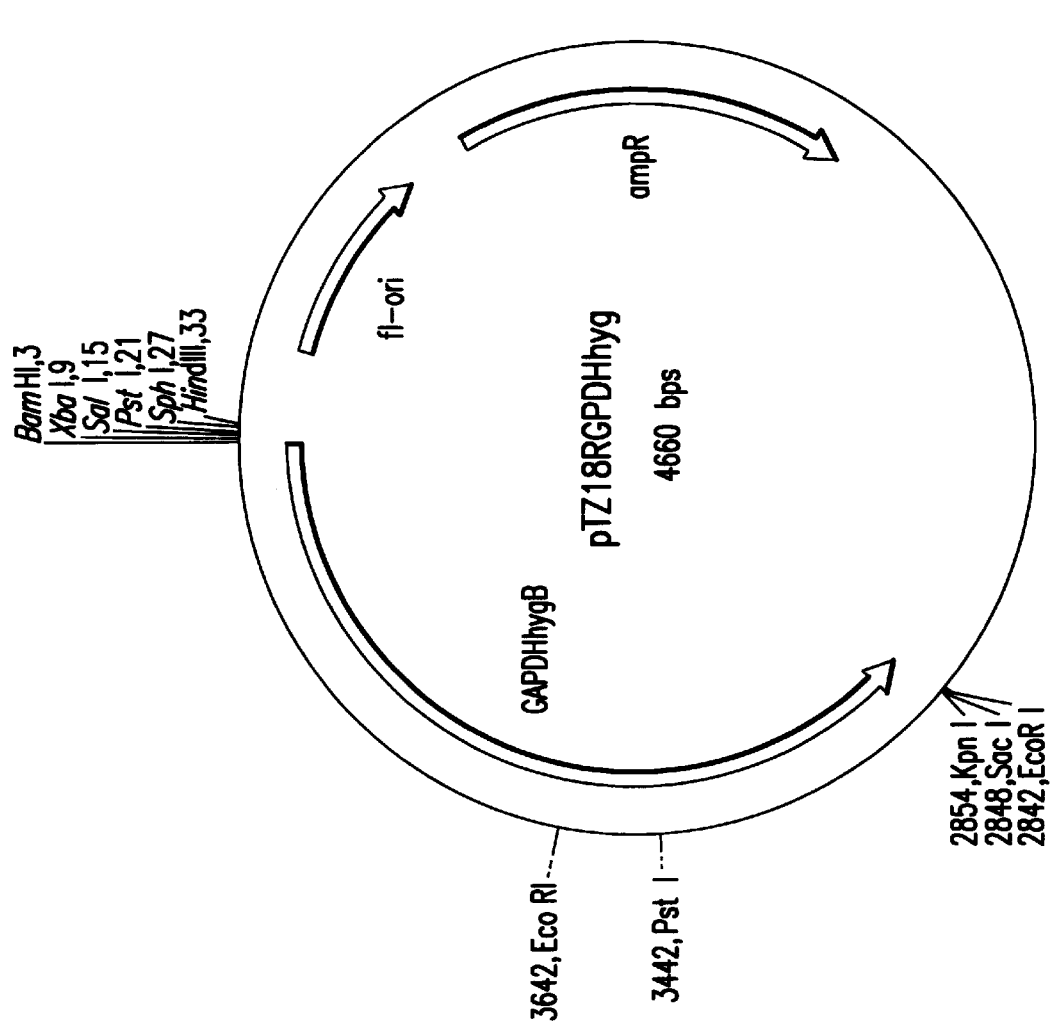
FIG. 1 shows the physical map of plasmid pTZ18RGAPDHhygB.

This plasmid contains a gene conferring resistance to the drug hygromycinB under control of the GAPDH-promoter. Said combination of DNA-fragments may be used as a dominant selectable marker in yeast.

pTZ18R (commercially available, Pharmacia) was cut with SmaI. A BamHI-SalI fragment, containing a gene conferring resistance against the drug hygromycinB, similar to that as described by Gritz and Davies (Gritz, L. and Davies, J (1983), Gene 25 179–188), under control of the GAPDH-promoter, similar to that as described by Holland and Holland (Holland and Holland, (1980), J.Biol.Chem. 255 2596–2605), was made blunt with the aid of large fragment Klenow DNA polymerase I. This blunt-ended fragment was ligated to pTZ18R, generating the plasmid pTZ18RGAPDHhygB (FIG. 1).

2) pKSP01

This integrative plasmid contains the HXT1-gene under control of the strong constitutive ADH1-promoter and a hygromycinB resistance gene under control of the GAPDH-promoter.

Figure 2:
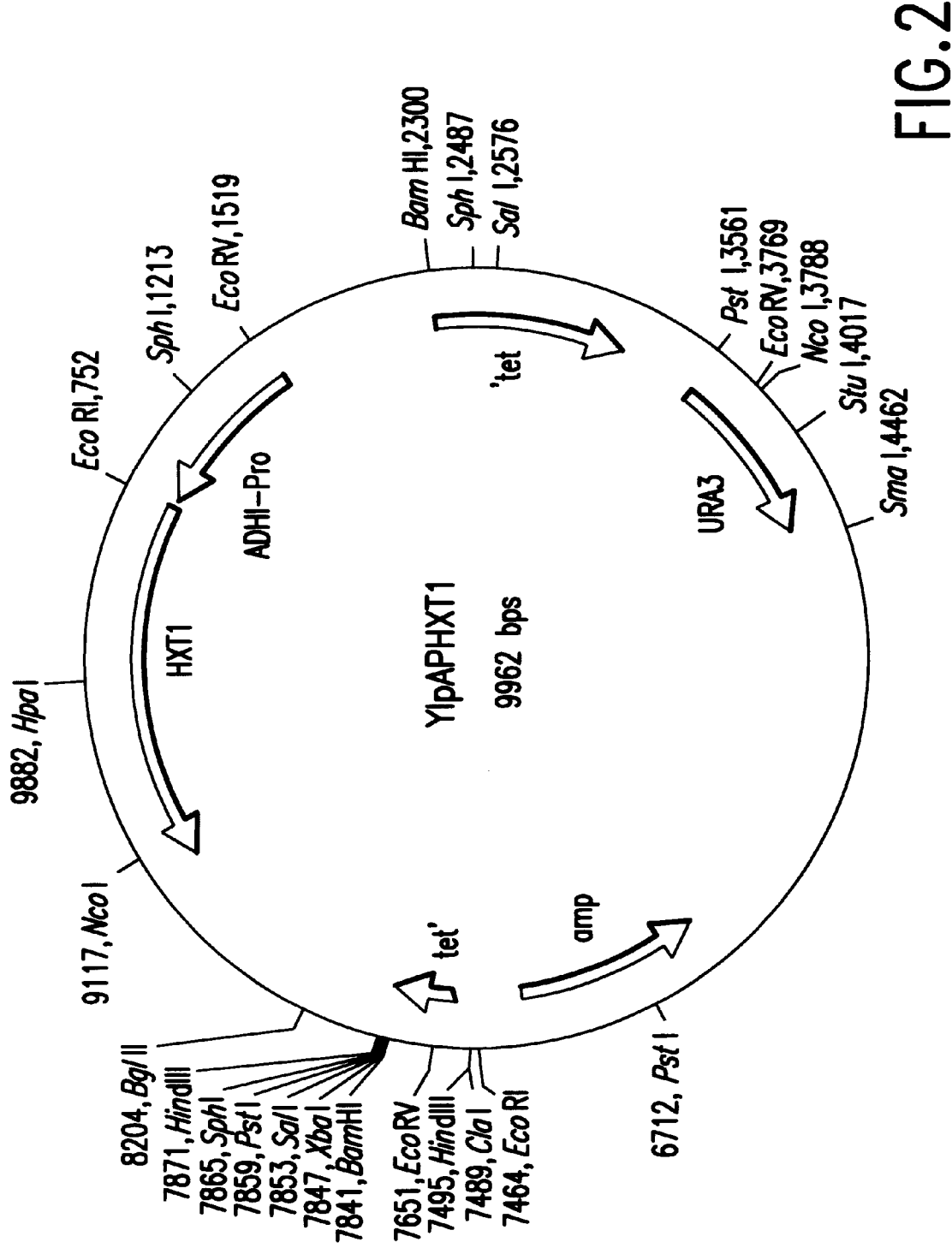
FIG. 2 shows the physical map of plasmid YIpAPHXT1.
Figure 3:
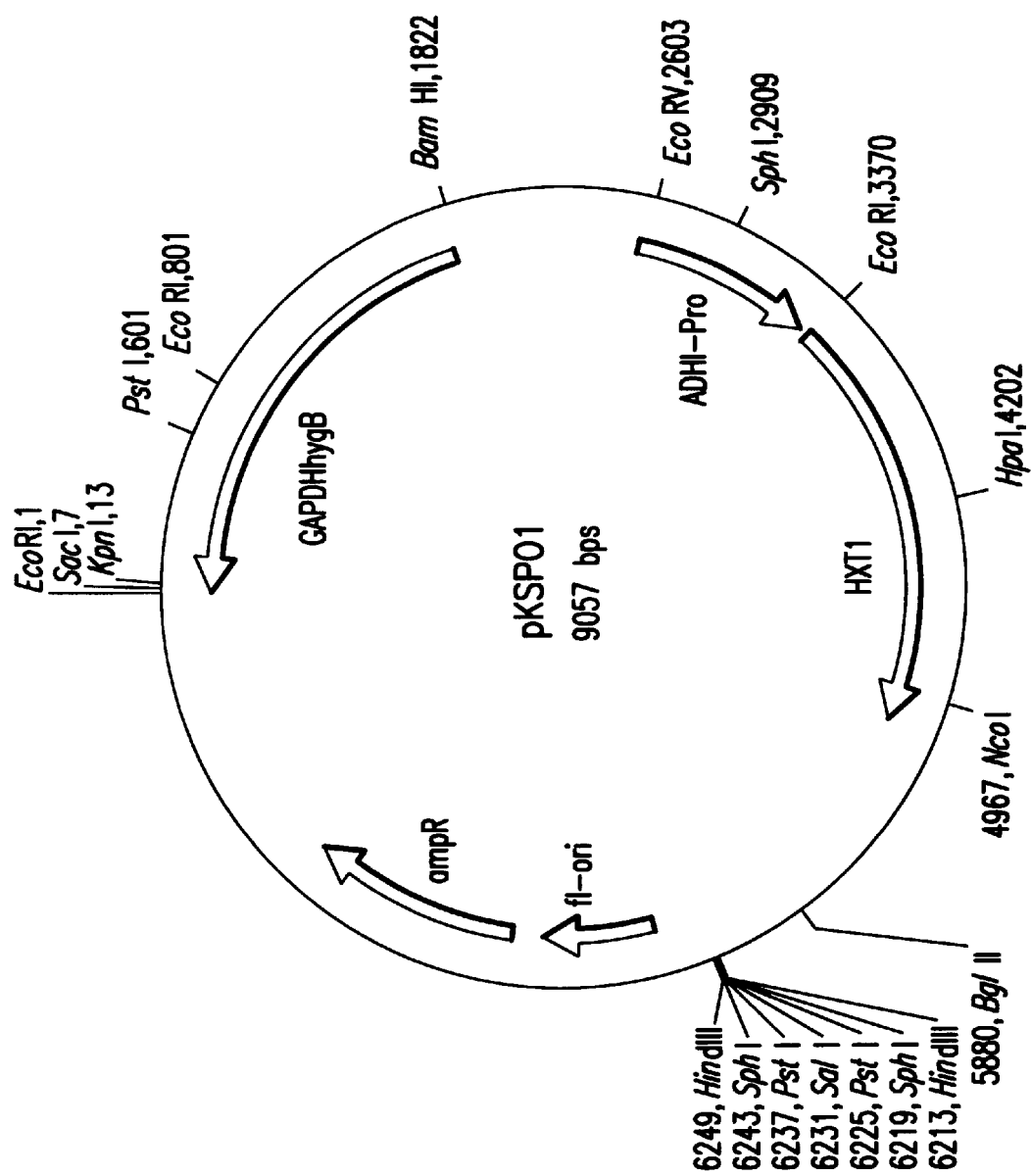
FIG. 3 shows the physical map of plasmid pKSP01.

Plasmid YIpAPHXT1 (FIG. 2, obtained from M.Ciriacy and E.Reifenberger, Heinrich-Heine University, Düsseldorf, Germany), containing the HXT1-gene under control of the ADH1-promoter, similar to that as described by Bennetzen and Hall (Bennetzen, J. C. and Hall, B. D. (1982) J.Biol.Chem 257, 3018), was cut with BamHI and SalI, generating, amongst others, a fragment of about 4.4 kb. This fragment was ligated into pTZ18RGAPDHhygB, previously cut with BamHI and SalI, generating the plasmid pKSP01 (FIG. 3).

This plasmid is a integrative plasmid, which integrates into the host cell's genome upon linearisation. In this case, the integration is directed to the HXT1-locus on the genome of the host cell by cutting pKSP01 with the restriction enzyme HpaI.

Yeast Transformation

Transformation of yeast strains was carried out according to the method of Ito et al (Ito, H., Fukuda, Y., Murata, K. and Kimura, A. (1983) J.Bacteriology 153 163–168). Saccharomyces strains are grown in a standard yeast nutrient medium to a density of 1 to 6 OD600 nm units. The yeast cells are harvested by centrifugation, washed and pretreated with alkali metal ions, preferably lithium salts, at concentrations up to 2 M, preferably 1 M. After incubating the cells for about 60 minutes at 30° C., the cells are incubated with the transforming DNA (1–20 μg) for about 60 minutes at 30° C. Polyethylene glycol is added, preferably polyethylene glycol of about 4000 daltons, at a final concentration of about 20% to 50%. After incubation for 30 minutes at 30° C., the cells are subjected to a heat treatment at 42° C. for 5 minutes. Desirably, the cell suspension is washed with a standard yeast nutrient medium, followed by incubation in an amount of fresh standard yeast nutrient medium. The cells are incubated for 1 hour at 30° C. and plated on standard agar media containing 400 μg hygromycinB/ml agar medium.

When yeast cells have been transformed with integrating plasmids, integration was directed to the HXT1-locus using HpaI-digested DNA. The integration event yields one or a few copies of the plasmid vector (Szostak, J. W. and Cou, R. (1979) Plasmid 2 536). The exact copy number in these transformants, used in $CO_2$-production experiments, has been determined using standard molecular biology techniques (Sambrook, J. et al, supra).

Determination of $CO_2$ Production in Synthetic Dough Medium (Test A)

Cells of the yeast *Saccharomyces cerevisiae* were grown on a YEP-medium (1% w/v yeast extract, 2% w/v peptone) containing 1% maltose. The cells were grown overnight in a rotary shaker at 30° C. until the cells were in stationary phase. The cells were harvested by centrifugation, washed with water and resuspended in water to a concentration of about 13–15 mg per ml. Subsequently, 0.6 ml of the yeast suspension was added to 1.9 ml of water and 2.0 ml of synthetic dough medium (composition per litre:110 g glucose, 3 g $(NH4)_2SO_4$, 4 g $MgSO_4 \cdot 7H_2O$, 4 g $KH_2PO_4$ 4 g casaminoacids, 4 g citric acid.1aq, 45 g trisodiumcitrate.2aq, 10 mg vitamin B1 and B6, 40 mg nicotinic acid, 20 mg calcium panthotenate and 0.02 mg biotin, at pH 5.6) and incubated at 28° C. for 165 minutes. The $CO_2$ produced during the incubation was flushed from the solution with carrier gas ($N_2$) and measured for 165 minutes using an infrared detector (Leybold-Heraeus). Total amounts of $CO_2$ produced anaerobically as well as specific $CO_2$ production rates were calculated on-line.

List of strains

| | |
|---|---|
| strain B | industrial baker's yeast strain |
| strain B-pKSP01D | industrial baker's yeast strain B transformed with plasmid pKSP01 |
| strain C | industrial baker's yeast strain |
| strain C-pKSP01A | industrial baker's yeast strain C transformed with plasmid pKSP01 |
| strain D | industrial baker's yeast strain |
| strain D-pKSP01K | industrial baker's yeast strain D transformed with plasmid pKSP01 |

The following strains have been deposited with the Centraal Bureau voor Schimmelcultures, Baarn, Holland:

*Saccharomyces cerevisiae* strain B has been deposited as strain 227 Ng with the CBS under the accession number 745.95,

*Saccharomyces cerevisiae* strain C has been deposited as strain 210 Ng with the CBS under the accession number 744.95,

*Saccharomyces cerevisiae* strain D has been deposited as strain 247 Ng with the CBS under the accession number 747.95.

EXAMPLE 1

Constitutive Expression of the HXT1-Gene Leads to Improved Gas Production Rates in Synthetic Dough Medium.

Figure 4:
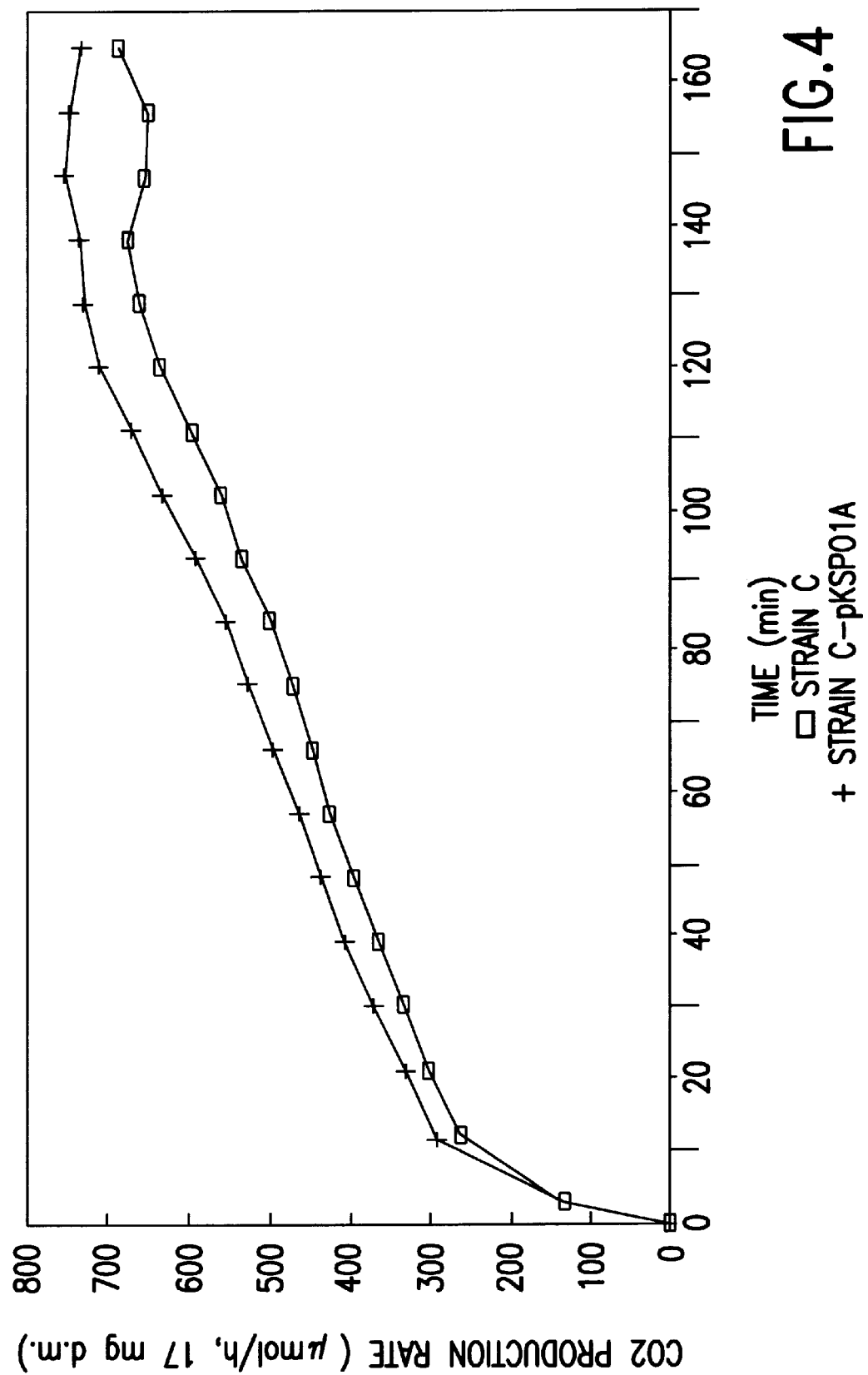
FIG. 4 shows the gas production rates of strain B and a transformant of strain B constitutively expressing Hxt1p.
Figure 5:
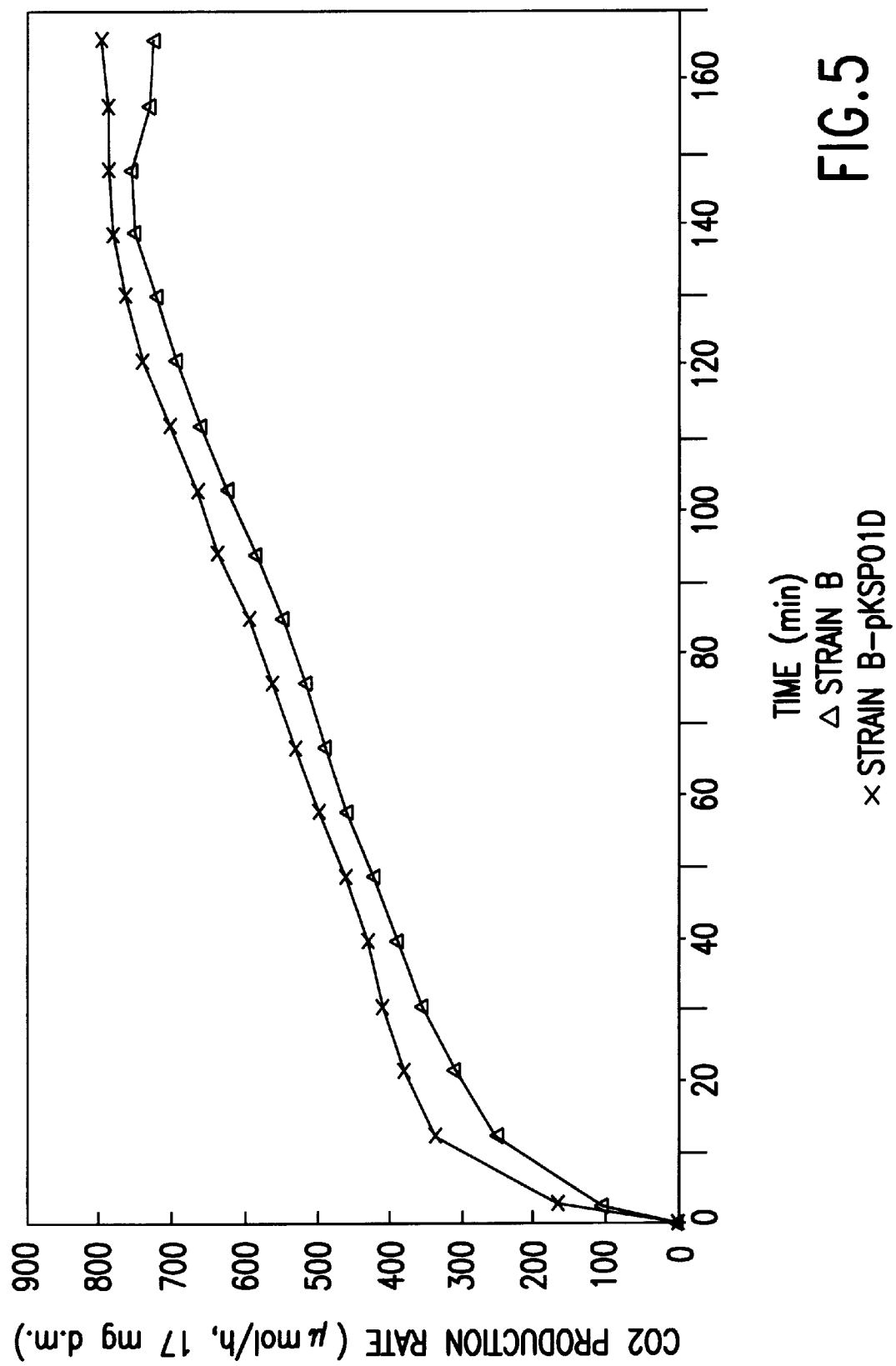
FIG. 5 shows the gas production rates of strain C and a transformant of strain C constitutively expressing Hxt1p.

Strains B, B-pKSP01D, C, C-pKSP01A, D and D-pKSP01K were grown overnight at 30° C. in a YEP-medium containing 1% maltose as a carbon source. The $CO_2$ production rates (FIGS. 4–6), as well as the total amount of $CO_2$ were measured in synthetic dough medium (table 1). The total amount of $CO_2$ produced under these circumstances increased significantly in the transformants compared to the respective parental strains.

TABLE 1 total $CO_2$-production of yeast strains, overexpressing the HXT1-gene, in synthetic dough medium (in ml $CO_2$ per 285 mg dry weight in 165 minutes) and the relative amounts of $CO_2$ produced by these yeast strains.

| strain | $CO_2$-production (ml $CO_2$/285 mg dry weight, 165 minutes) | relative $CO_2$-production (%) |
| --- | --- | --- |
| strain B | 618 | 100 |
| strain B-pKSP01D | 673 | 109 |
| strain C | 556 | 100 |
| strain C-pKSP01A | 619 | 111 |
| strain D | 528 | 100 |
| strain D-pKSP01K | 599 | 113 |

What is claimed is:

1. A transformed industrial non-haploid yeast strain characterized as having enhanced $CO_2$ and ethanol production rates relative to the untransformed parent yeast strain consisting essentially of one or more hexose transporter genes under the control of a strong constitutive promoter, wherein the hexose transporter gene is HXT1, HXT2, HXT3, HXT4, HXT5, HXT6 or HXT7 and the enhanced $CO_2$ production would be more than 500 ml of $CO_2$ per 285 mg dry matter in 165 minutes.

2. The transformed yeast according to claim 1 wherein the yeast is capable of immediately expressing the hexose transporter gene under conditions wherein there is delayed expression of this gene by a wild type yeast strain.

3. The transformed yeast according to claim 1 wherein the hexose transporter gene and constitutive promoter are homologous to the yeast.

4. The transformed yeast according to claim 1 which belongs to the genus Saccharomyces.

5. The transformed yeast according to claim 1 which is a beer, baker's, wine or whisky yeast.

6. The transformed yeast according to claim 1 in the form of active dry, instant dry, compressed or cream yeast.

7. A process of producing a transformed yeast as defined in claim 1 which process comprises transforming a yeast belonging to an industrial yeast strain in such a way as to provide said yeast with one or more hexose transporter genes selected from HXT1, HXT2, HXT3, HXT4, HXT5, HXT6 or HXT7 which are constitutively expressed under the control of a strong constitutive promoter.

8. The transformed yeast of claim 4 which is a strain of *Saccharomyces cerevisiae*.

9. The transformed yeast of claim 1 wherein the transformed yeast has an enhanced hexose membrane transport rate relative to the hexose membrane transport rate of a yeast that does not constitutively express a hexose transporter gene.

10. A process of producing the transformed industrial non-haploid yeast strain of claim 1, belonging to the genus Saccharomyces and having improved $CO_2$ and ethanol production rates, to increase $CO_2$ production or to enhance hexose membrane transport over that of a wild type yeast strain which process comprises transforming a yeast belonging to an industrial yeast strain in such a way as to provide said yeast with one or more hexose transporter genes selected from HXT1, HXT2, HXT3, HXT4, HXT5, HXT6 or HXT7 which are constitutively expressed under the control of a strong constitutive promoter.

* * * * *